United States Patent [19]
Grey et al.

[11] Patent Number: 5,485,267
[45] Date of Patent: Jan. 16, 1996

[54] ZEEMAN EFFECT SPECTROMETER HAVING HIGH-SPEED ELECTROMAGNETIC SWITCHING CAPABILITY

[75] Inventors: Ronald G. Grey, Beaumaris; Clive T. Davenport, Patterson Lakes; John T. Huberts, Menzies Creek, all of Australia

[73] Assignee: GBC Scientific Equipment Pty. Ltd., Dandenong, Australia

[21] Appl. No.: 145,095

[22] Filed: Nov. 3, 1993

[30] Foreign Application Priority Data

Nov. 5, 1992 [AU] Australia ................................ PL5666

[51] Int. Cl.$^6$ ........................................................ G01J 3/36
[52] U.S. Cl. ............................................................ 356/307
[58] Field of Search ............................................... 356/307

[56] References Cited

U.S. PATENT DOCUMENTS 4,341,470  7/1982  Parker et al. ............................. 356/304

FOREIGN PATENT DOCUMENTS 1271170  4/1972  United Kingdom .
8910025  10/1989  WIPO .

*Primary Examiner*—Vincent P. McGraw
*Assistant Examiner*—K. P. Hantis
*Attorney, Agent, or Firm*—Cushman Darby & Cushman

[57] ABSTRACT

A spectrometer using Zeeman background correction is disclosed which has a sample producer (100) for producing a cloud of atoms, an electromagnetic radiation source (102) for irradiating the atom cloud, a detector (104) for detecting the radiation after it passes through the atom cloud and an electromagnet (14) for applying a magnetic field to the atom cloud. A power supply and switching unit (106) for powering the electromagnet and switching the electromagnet on and off to create a Zeeman effect are provided. The switching unit has transistors (16–22, 40, 42, 50, 52) controlled by a control circuit (25), and the power supply includes a rectifier (10) and one or more capacitors (12, 12a, 12b). The switching time is typically on the order of 1–1.5 ms or less and the high voltage which is applied is on the order of 400–800 V.

7 Claims, 5 Drawing Sheets

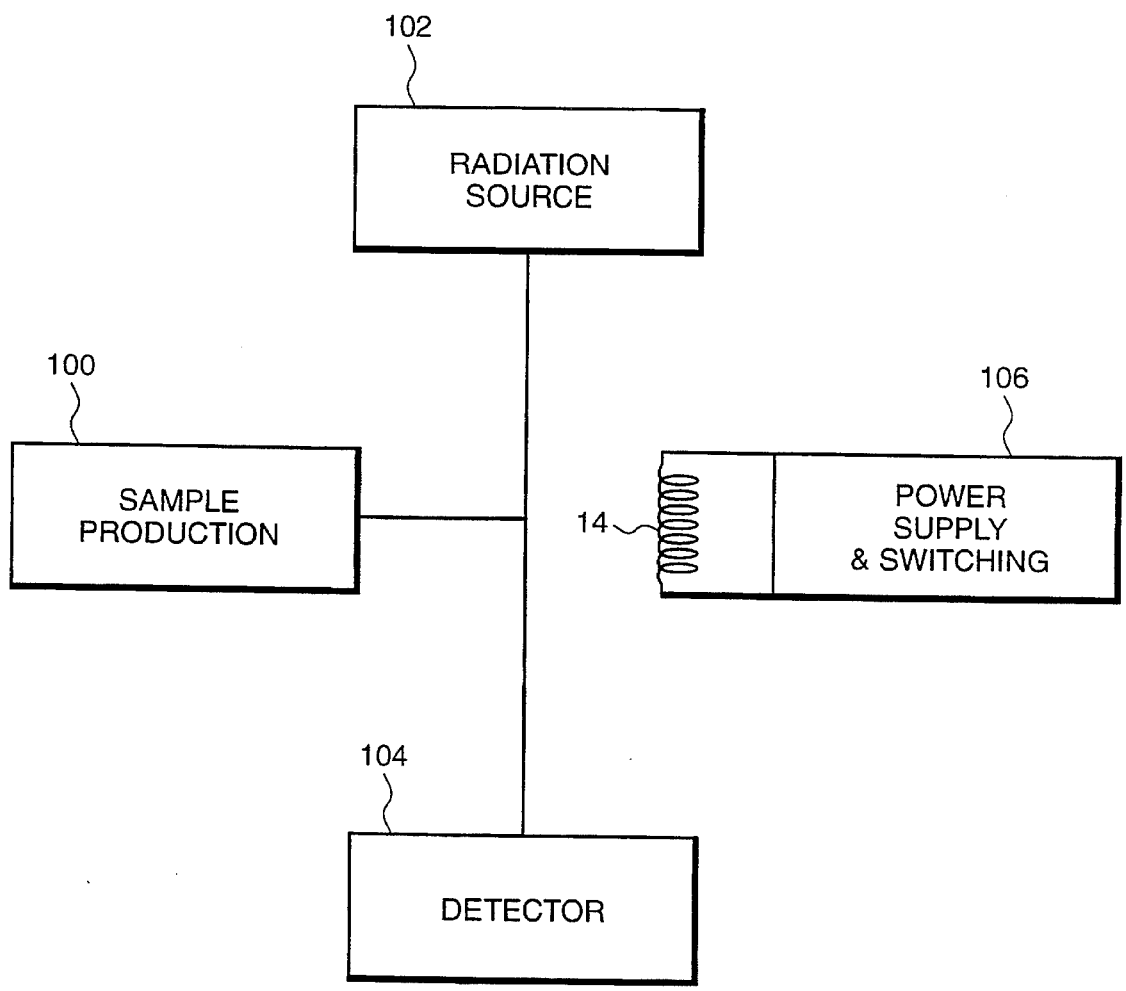

ZEEMAN EFFECT SPECTROMETER HAVING HIGH-SPEED ELECTROMAGNETIC SWITCHING CAPABILITY

BACKGROUND OF THE INVENTION

1. Field of the Invention

This invention relates to spectrometers and in particular to atomic absorption spectrometers which use the Zeeman effect for background correction.

2. Description of the Related Art

Atomic absorption spectrometers are used to determine the amount or concentration of an element in a sample material. The sample which is to be analysed is atomized to produce a cloud of atoms for analysis. A beam of light from a light source is directed through the cloud of atoms and is detected. Light is absorbed by the atoms in the cloud at wavelengths which are characteristic of the element being determined. However, absorption of the measuring light beam is not only caused by the atoms which are to be analysed but also by other sources which produce background absorption which has to be corrected in order to provide accurate measurement of the atomic absorption.

The Zeeman effect is used for background correction. This technique uses a magnetic field which is applied to the atoms in the cloud or in the light source to split and shift the absorption lines of the atoms or emission lines of the source. The shifting of the absorption lines of the atoms ensures that they no longer coincide with the spectral lines of the measuring light beam and this permits discrimination between atomic absorption caused by the atoms and background absorption.

Spectrometers which employ the Zeeman effect utilise an electromagnet which is typically powered by sinusoidal current from power mains, as shown in FIG. 1A. More recently a square wave is driven onto coils of the electromagnet and background absorption measurements are made when the electromagnet is turned on and measurements of total absorption (atomic plus background) are made when the electromagnet is turned off. FIG. 1B.

We have discovered that conventional atomic absorption spectrometers utilising the Zeeman effect produce a magnetic field which changes slowly between switching on and off of the electromagnetic so that there is a significant time delay between the period in which atomic absorption is measured and the period in which total absorption is measured thereby resulting in a significantly large dead time between measurements.

The slow change in magnetic field is illustrated with reference to FIG. 1A and 1B. Background absorption is measured in time period A. Total absorption is measured in time period B. The time period C between periods A and B is the dead time which is not normally used for measurement.

We have identified a number of significant problems which result from the dead time referred to above.

The disadvantages may be summarised as follows:

1. Poor background correction due to the significant time difference between making background absorption measurement and a total absorption measurement in situations where the background absorption changes with time. Since the background absorption changes with time the background absorption taking place at the times of the background absorption measurement and the total absorption measurement can be significantly different thereby giving incorrect background correction.
2. Measurement time efficiency is poor due to the delay caused by the changing magnetic field in which no atomic absorption measurement or background measurement can be made.
3. Since the time during which measurements can be made is small, high peak lamp currents must be used in order to achieve acceptable noise levels. The high peak lamp currents result in poorer sensitivity of the spectrometer and reduced 1 amp life.

SUMMARY OF THE INVENTION

We have found that minimising the time in which the magnetic field changes and increasing the frequency, overcome all of the disadvantages referred to above.

The invention may therefore be said to reside in a spectrometer using Zeeman background correction including:

sample producing means for producing a cloud of atoms for analysis;

a source of electromagnetic radiation for producing a beam of radiation for application to the atom cloud;

a detector for detecting the beam of electromagnetic radiation after it passes through the atom cloud;

an electromagnet for applying a magnetic field to the cloud of atoms or the source of electromagnetic radiation;

switching means for switching on and off the electromagnet periodically to create a Zeeman effect to compensate for background absorption; and power supply means for powering the electromagnet such as to produce a changing magnetic field in which the change between when the electromagnet is switched on and when the electromagnet is switched off is minimum in time.

By minimising the time period in which the magnetic field changes, improved background correction is obtained because the atomic absorption measurement and the background measurement are much closer to simultaneous measurements and therefore any change in background absorption between those measurements is minimised. Measurement efficiency is increased in view of the small time period between measurements. Peak currents applied to the source for producing electromagnetic radiation can be reduced and the increased duty cycle; thereby increasing lamp life. Finally, the reduced peak current also increases sensitivity of the instrument.

Preferably a switching time of 1 to 1.5 ms or less is utilised.

Preferably the power supply applied to the electromagnet is such as to produce a magnetic field which is as close to a square wave as possible. Typically, the voltage applied to the electromagnet is in the order of 400 to 800 volts.

Preferably the means for producing the cloud of atoms for analysis comprises an electrothermal atomizer.

Preferably the switching means for switching the electromagnet on and off comprises at least two transistors and two diodes.

Preferably at least one capacitor is arranged in parallel to the electromagnet for storing energy and returning that energy to the electromagnet. Thus, the power supply need only make up losses which result from the cycling of the power from the capacitor to the electromagnet.

Preferably the spectrometer includes a rectifier for rectifying mains AC voltage to produce a direct current voltage.

The direct current voltage is high enough to allow the magnetic field to change rapidly which therefore minimises the dead time between measurements and thus maximises the measurement duration thereby allowing high frequency and high speed operation.

In order to attain a nearly square wave magnetic field the following conflicting conditions must be satisfied.

a) To obtain the necessary magnetic flux of approximately 1 tesla, a very high number of ampere turns (typically 15,000 to 20,000) is required.

b) High ampere turns requires a large number of turns on the electromagnet and a large current.

c) A large number of turns produces a large L (Inductance) value which reduces (limits) the rate of change of current for a given voltage.

The solution to points a, b & c is to use a very high voltage (typically 400 to 800 volts) to drive the electromagnet.

BRIEF DESCRIPTION OF THE DRAWING

Preferred embodiments of the invention will be described, by way of example, with reference to the accompanying drawings in which:

FIG. 1E is a block diagram showing a spectrometer according to the/preferred embodiment of the invention;

DETAILED DESCRIPTION OF THE PRESENTLY PREFERRED EXEMPLARY EMBODIMENTS

Figure 1A:
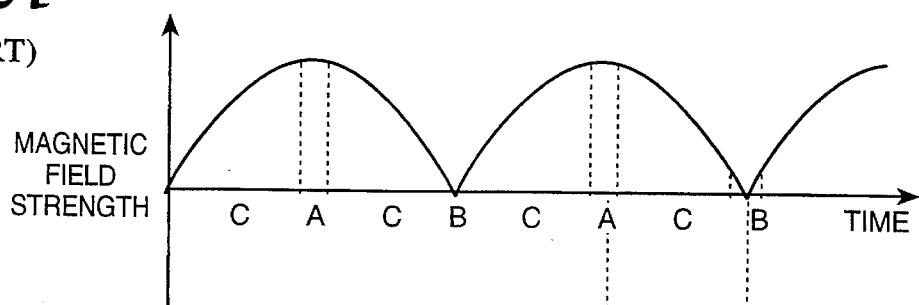
FIG. 1A and 1B are views showing a wave forms of magnetic field according to conventional spectrometers.
Figure 1B:
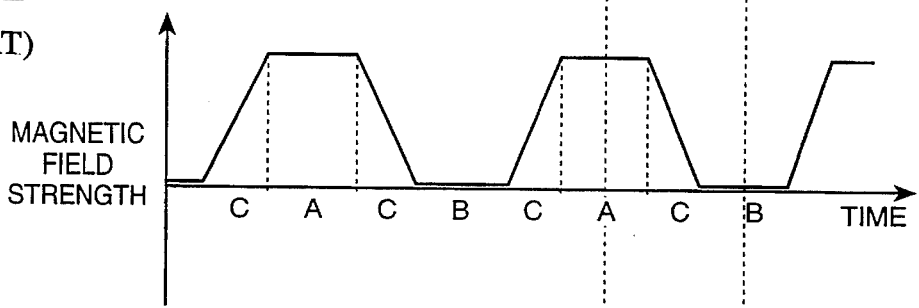

With reference to FIG. 1E, a block diagram showing the general layout of a spectrometer according to the present embodiment is shown. The spectrometer generally comprises a sample producer 100 for producing a cloud of atoms for analysis. A source of electromagnetic radiation 102 produces a beam of radiation for application to the atom cloud and a detector 104 detects the radiation after it passes through the atom cloud. An electromagnet 14 for applying a magnetic field to the cloud of atoms is controlled by a power supply and switching means 106.

Figure 1C:
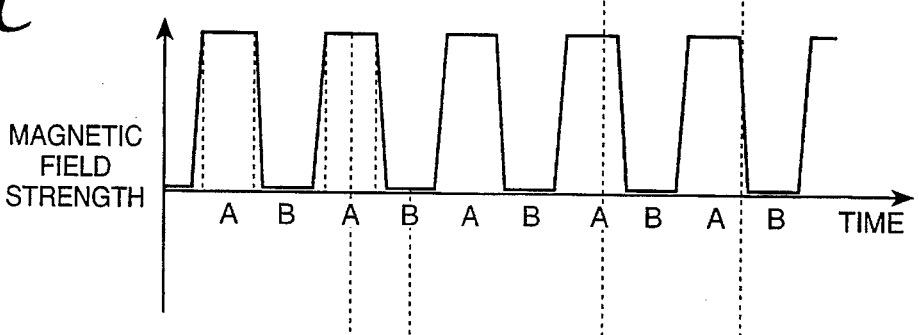
FIG. 1C is a graph showing a wave form of magnetic field according to the preferred embodiment of the invention.
Figure 1D:
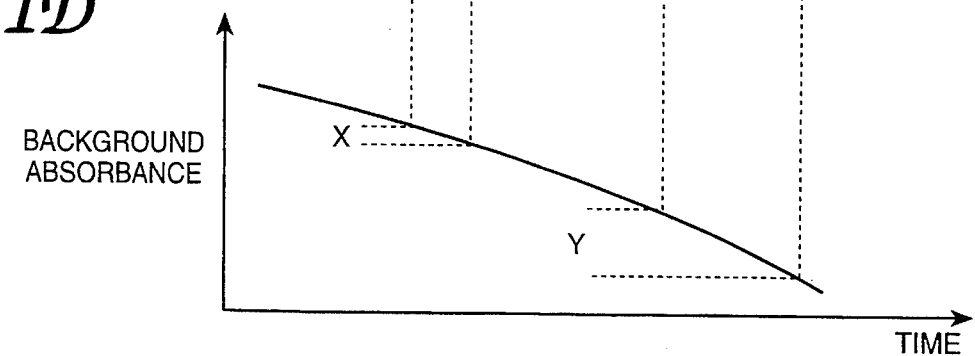
FIG. 1D shows the improvement in the measurement of a changing background absorbance signal due to the preferred embodiment of the invention.
Figure 2:
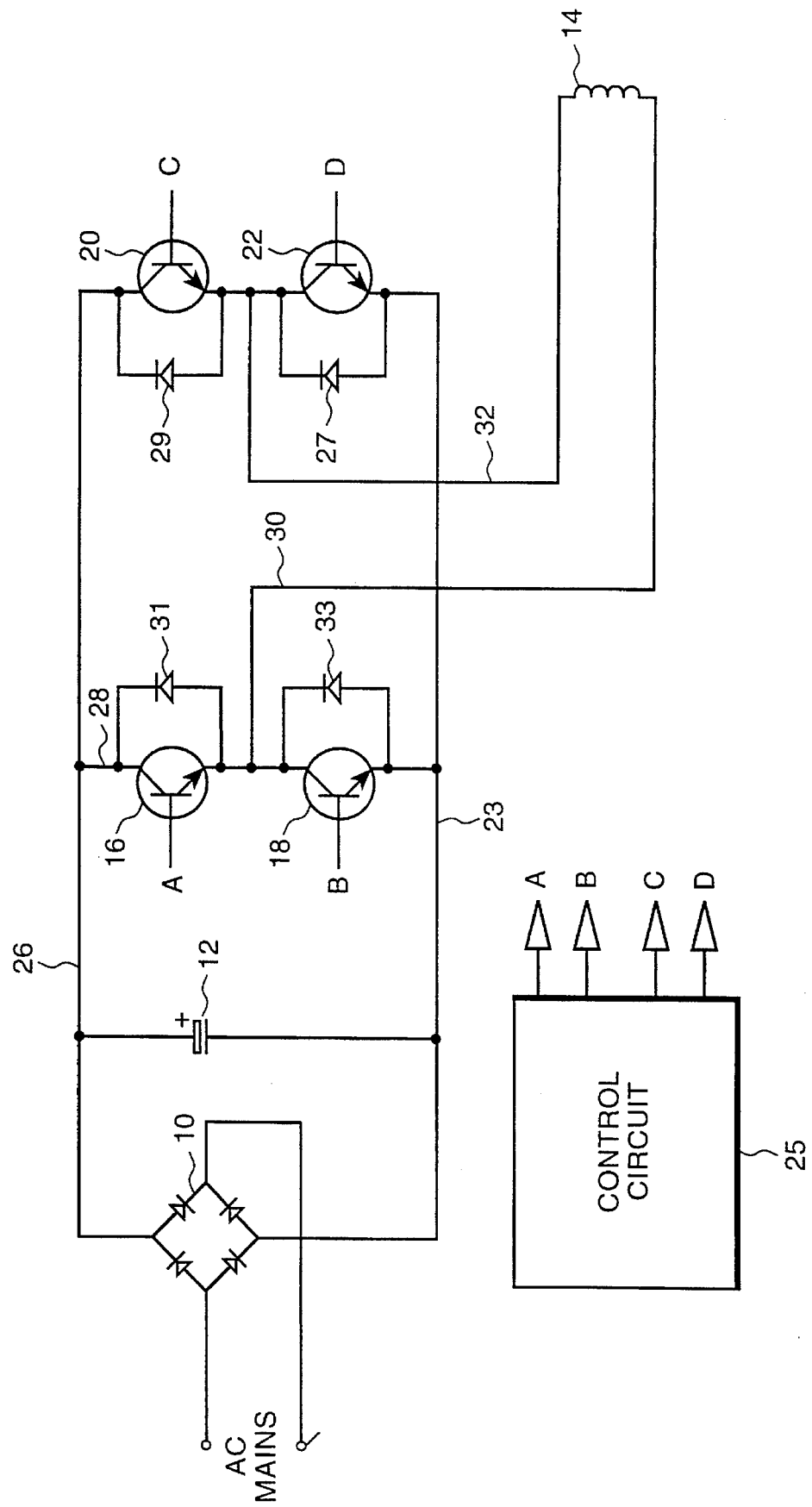
FIG. 2 shows a circuit according to one embodiment of the invention.

With reference to FIG. 2 which shows the first embodiment of the power supply and switching means 106, AC mains voltage is applied to a rectifier 10 for rectifying the voltage into direct current voltage. A capacitor 12 is arranged in parallel with the rectifier 10 and is also arranged parallel to magnetic coil 14 of an electromagnet (not shown) which applies a magnetic field to a cloud of sample atoms (not shown) generated by a electrothermal atomizer (not shown) or the like. Four transistors 16, 18, 20 and 22 are arranged in series with the capacitor 12 and magnetic coil 14 and comprise switches for switching the power supply through magnetic coil 14 for switching the magnetic coil on and off to produce a changing magnetic field. A control circuit 25 is provided for producing signals which are applied to the bases of the transistors 16 to 22 for selectively switching transistors on and off so that a direct voltage stored in the storage capacitor 12 can discharge through the transistors to the magnetic coil 14 to generate the magnetic field. Diodes 27, 29, 31 and 33 are arranged parallel to transistors 16 to 22. For example, when transistors 16 and 22 are switched on by control circuit 25 capacitor 12 discharges through line 26, line 28, transistor 16, line 30, magnetic coil 14, line 32 and transistor 22. When transistor 16 is turned off the current in the magnet coil is maintained and flows through transistor 22 and diode 33. When transistor 22 is turned off the magnetic coil 14 discharges through those diodes 29 and 33 so that the storage capacitor 12 is recharged. The voltage applied and stored in capacitor 12 is typically in the order of 400 to 800 volts or of sufficient level to ensure that the magnetic field is as near as possible to a square wave form as shown in FIG. 1C. Thus, atomic absorption measurements may be made in time period A and total absorption measurements made in time period B. Since the magnetic field is close to a square wave form the dead time C between measurements is negligible thereby ensuring that background measurements and total absorption measurements are made as close to simultaneous as possible. As is shown in FIG. 1D, and also with reference to FIG. 1, if the background level is changing the preferred embodiment of the invention ensures that a total absorption measurement and background measurement are made as close together as possible thereby reducing any error due to the changing background as shown by value X in FIG. 1D. This is compared to the large error Y which is produced according to the prior art where the magnetic field changes slowly and there is a larger dead time C between atomic absorption measurements in time period A and background measurements in time period B.

Figure 3:
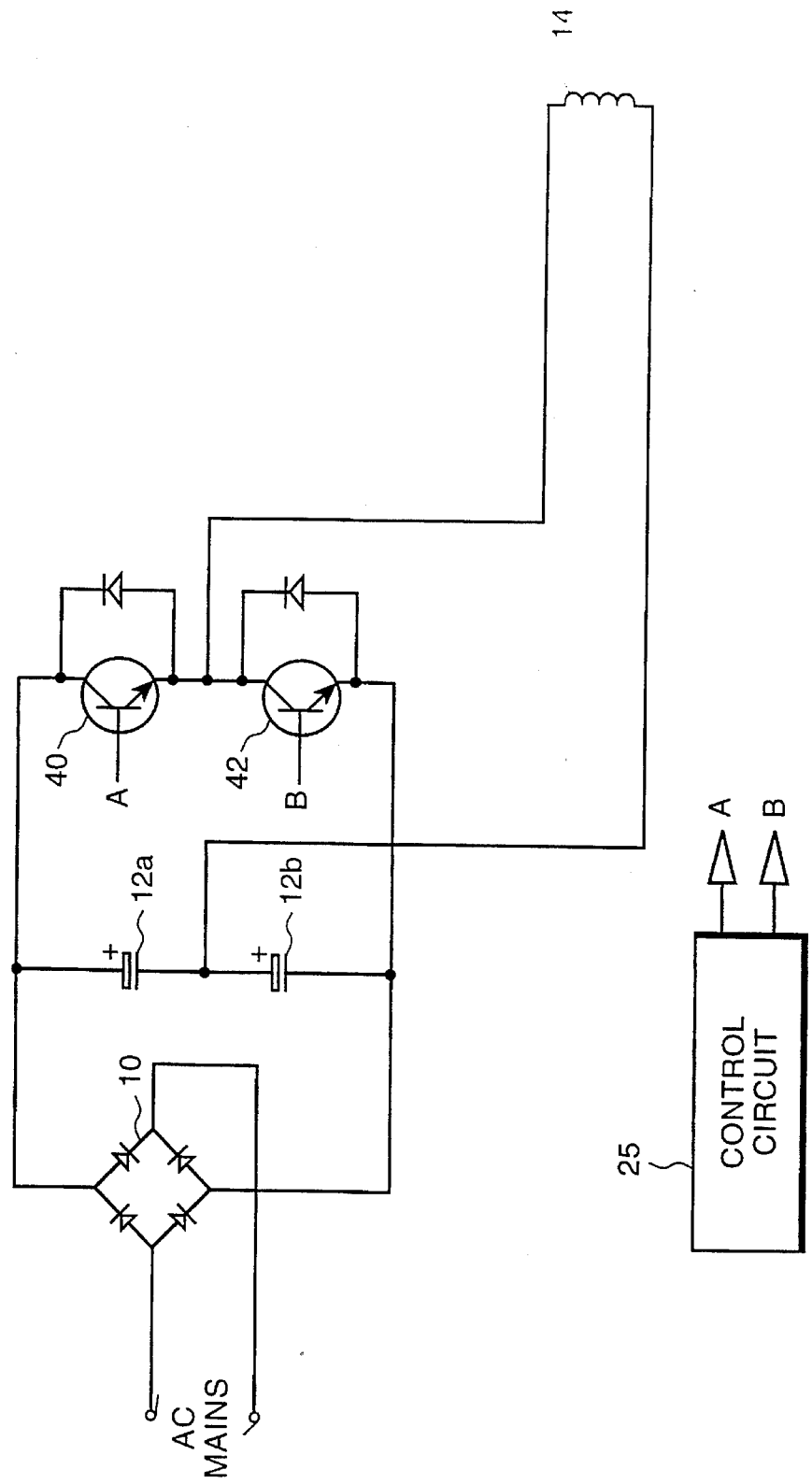
FIG. 3 shows a circuit according to a second embodiment.

FIG. 3 shows a second embodiment of the invention which comprises two storage capacitors 12a and 12b and two transistors 40 and 42. Control circuit 25 switches on and off transistors 40 and 42 so that the storage capacitors 12b can discharge through the transistors to energise the magnetic coil 14 and allow the magnetic filed to collapse and recharge the storage capacitors. Once again, the voltage applied is sufficient to ensure the square wave form as shown in FIG. 1C.

Figure 4:
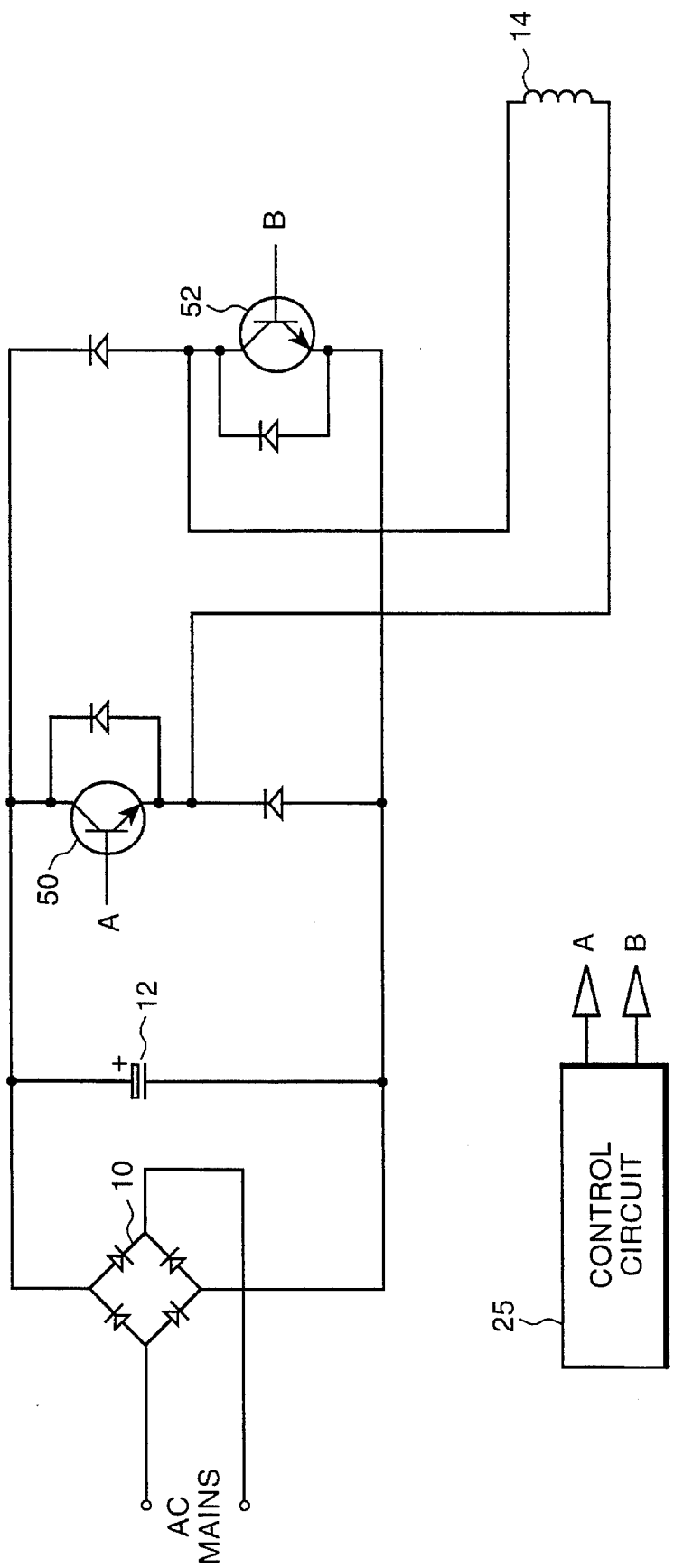
FIG. 4 shows a circuit according to a third embodiment.

FIG. 4 shows a still further embodiment in which a single storage capacitor 12 is provided and two transistors 50 and 52 are provided. The control circuit 25 controls the transistors 50 and 52 so that the storage capacitor can discharge through the transistors to energise the magnetic coil 14 and allow the magnetic field to collapse by recharging the storage capacitor 12.

Thus, the direct voltage which is generated from the AC supply voltage is high enough to allow the magnetic field to change rapidly thus maximising the measurement duration and allowing high frequency operation. The energy supplied from the direct voltage is stored in the reservoir capacitors 12, 12a, 12b etc. and this allows operation at a frequency higher than that of the AC supply voltage. A small portion of the energy stored in the reservoir capacitors is cycled between the reservoir capacitors and the coil 14 by switching the direct voltage by means of the transistors 16 to 22, 40, 42, 50, 52. Energy lost from the reservoir capacitors due to heating of the switching devices and coil 14 is replaced by the AC supply voltage and the rectifier for converting the supply voltage into a direct voltage.

The sensitivity of the spectrometer and in particular signal to noise ratio improves by square root of 2 as measurement time doubles.

Since modifications within the spirit and scope of the invention may readily be effected by persons skilled within the art, it is to be understood that this invention is not limited to the particular embodiment described by way of example hereinabove.

The claims defining the invention are as follows:

1. A spectrometer using Zeeman background correction including:

sample producing means for producing a cloud of atoms for analysis;

a source of electromagnetic radiation for producing a beam of radiation for application to the atom cloud;

a detector for detecting the beam of electromagnetic radiation after it passes through the atom cloud;

an electromagnet for applying a magnetic field to the cloud of atoms or the source of electromagnetic radiation;

switching means for switching on and off the electromagnet periodically to create a Zeeman effect to compensate for background absorption; and power supply means for powering the electromagnet with a high voltage such as to produce a changing magnetic field in which the change between when the electromagnet is switched on and when the electromagnet is switched off is minimum in time;

wherein the high voltage is in the range of 400 to 800 volts and a switching time for switching on and off the electromagnet is less than 1.5 ms.

2. The spectrometer of claim 1 wherein the power supply applied to the electromagnet is such as to produce a magnetic field which is as close to a square wave as possible.

3. The spectrometer of claim 1 wherein the means for producing the cloud of atoms for analysis comprises an electrothermal atomizer.

4. The spectrometer of claim 1 wherein the switching means for switching the electromagnet on and off comprises at least two transistors and two diodes.

5. The spectrometer of claim 1 wherein at least one capacitor is arranged in parallel to the electromagnet for storing energy and returning that energy to the electromagnet.

6. The spectrometer of claim 1 including:

a rectifier for rectifying mains AC voltage to produce a direct current voltage;

wherein the direct current voltage is high enough to allow the magnetic field to change rapidly which therefor minimises the dead time between measurements and thus maximises the measurement duration thereby allowing high frequency and high speed operation.

7. The spectrometer of claim 1 wherein the switching time is 1 to 1.5 ms.

* * * * *